(12) United States Patent
Harpaz

(10) Patent No.: US 12,211,612 B2
(45) Date of Patent: Jan. 28, 2025

(54) SYSTEM FOR IDENTIFYING AND TRACKING TOOLS, INSTRUMENTS AND CONSUMABLE PLACED ON WORKSURFACES

(71) Applicant: TrackiMed Ltd., Tel Mond (IL)

(72) Inventor: Itzhak Harpaz, Tel Mond (IL)

(73) Assignee: TrackiMed Ltd., Tel Mond (IL)

( * ) Notice: Subject to any disclaimer, the term of this patent is extended or adjusted under 35 U.S.C. 154(b) by 370 days.

(21) Appl. No.: 17/650,412

(22) Filed: Feb. 9, 2022

(65) Prior Publication Data
US 2022/0270749 A1    Aug. 25, 2022

Related U.S. Application Data

(60) Provisional application No. 63/147,764, filed on Feb. 10, 2021.

(51) Int. Cl.
| | | |
|---|---|---|
| *G06T 7/00* | (2017.01) | |
| *G06T 7/20* | (2017.01) | |
| *G06V 10/70* | (2022.01) | |
| *G06V 20/00* | (2022.01) | |
| *G16H 40/20* | (2018.01) | |

(52) U.S. Cl.
CPC ............... *G16H 40/20* (2018.01); *G06T 7/20* (2013.01); *G06V 10/70* (2022.01); *G06V 20/00* (2022.01); *G06T 2207/20081* (2013.01); *G06V 2201/034* (2022.01)

(58) Field of Classification Search
CPC .......... G16H 40/20; G16H 20/40; G06T 7/20; G06T 2207/20081; G06V 10/70; G06V 20/00; G06V 2201/034; G06V 20/52
See application file for complete search history.

(56) References Cited

U.S. PATENT DOCUMENTS

| | | | |
|---|---|---|---|
| 10,765,563 B2* | 9/2020 | Dein | A61B 50/20 |
| 2004/0186683 A1* | 9/2004 | Farber | G06Q 10/087 606/1 |
| 2021/0030483 A1* | 2/2021 | Jin | G06T 7/143 |
| 2022/0108789 A1* | 4/2022 | Shelton, IV | H04L 67/12 |

OTHER PUBLICATIONS

C. Perez-Vidal A,?, E. Carpintero a, N. Garcia-Aracil a, J.M. Sabater-Navarro a, J.M. Azorin a, A. Candela b, E. Fernandez a,c. Robotics and Autonomous Systems: "Steps in the development of a robotic scrub nurse". Sep. 20, 2011. www.elsevier.com/locate/robot.

* cited by examiner

*Primary Examiner* — Ping Y Hsieh
(74) *Attorney, Agent, or Firm* — M&B IP Analysts, LLC

(57) ABSTRACT

A system comprises a plurality of sensors adapted to identify and track items, e.g., tools, instruments and consumables, placed on worksurfaces. Each worksurface may contain one or more of these items and is used in an operating room. It is first determined if all the necessary items are available for a task at hand, then as items are removed, added or consumed a tally is updated to ensure that each is accounted for. When the task ends all items have to be accounted for by having the sensors review the content of the worksurfaces and identifying any discrepancy. In one embodiment, the system learns a process, e.g., a surgical process, such that in future cases it provides alerts of missing items before and after the task, provide instructions to equipment such as robots to assist in the task performance, and the like.

29 Claims, 3 Drawing Sheets

SYSTEM FOR IDENTIFYING AND TRACKING TOOLS, INSTRUMENTS AND CONSUMABLE PLACED ON WORKSURFACES

CROSS-REFERENCE TO RELATED APPLICATIONS

This application claims the benefit of U.S. Provisional Application No. 63/147,764 filed on Feb. 10, 2021, the contents of which are hereby incorporated by reference.

TECHNICAL FIELD

The present disclosure relates generally to tools placed within a worksurface, and more particularly to systems and methods for learning, identifying and tracking the tools as they are placed in or removed from a tools' worksurface.

BACKGROUND

In many jobs various tools, instruments as well as consumables are placed on worksurfaces, for example tables, benches, workspace, trays, containers, receptacles, pallets and the like, for the purpose of being used by one or more professionals. Depending on the type of task being performed, and the tools, instruments and/or consumables being used, identification, tracking and reporting may be of high importance for a variety of reasons, such as safety, effectiveness, and economy.

One such examples are operating rooms which are a major revenue source of hospitals globally. The life cycle of a medical surgery operation includes a variety of operational supporting processes: counting instruments, tracking sponges and pads, documenting, cleaning, planning and more. Those processes involve intensive human-labor, with minor formalization of those proficiencies, which causes that most of the know-how is based on human-centric experience.

These kinds of tracking of contents of worksurfaces that are performed by humans, are routinely performed over and over as part of the support tasks in, for example, clinical procedures. Often these are performed by stressed-out personnel, which eventually causes quality-gaps that either risk a patient, causes a task to be performed at a lesser quality level than is desirable, or causes waste of resources. In certain cases, worksurfaces such as a worksurface shown in FIG. 1, may be loaded with a variety of items, in this particular case, surgical instruments. In other cases, items may include combinations of instruments, tools, consumables and other matter that is required to perform, for example, a surgery.

In order to ease on the staff a trend has been developing to make use of robots in assisting in the laborious procedures. For example, in surgical operation routines dedicated robots may be used to assist the medical team in all the peripheral tasks within the operating room. This may include the delivery of instruments and equipment, tracking and counting used instruments and disposing of devices, cleaning the operating room and preparing it for the next scheduled surgery. However, for bringing such robots to operate effectively and efficiently it is necessary to record a vast number of undocumented procedures and transforming them into a structured scheme that will be the operation room ontology foundation for decision making algorithms and task recommendations running the supporting operation room robot.

A challenge of, for example the operating room, or places where tasks are performed using worksurfaces containing equipment, instruments, and consumables, is to account for differences in similar tasks, for example an appendix removal from a patient, and recognizing that in different operating rooms, and in different situations, there may be differences, sometimes significant, that require use of different tools or practices, with different amounts of consumable. Even in the same operating room, performing the same procedure, may be different depending on a particular situation. Current solutions do not provide the necessary agility to address such differences and timely alert the staff of potential discrepancies or requirements as the procedure progresses.

It would therefore be advantageous to provide a solution that overcomes the deficiencies of deployment of robotic systems. It would be further beneficial if such a system could assist in formalization of the provision and tracking of instruments, tools and consumables that are placed in a worksurface, or worksurfaces, and provide comparison across a plurality of operating rooms.

SUMMARY

A summary of several example embodiments of the disclosure follows. This summary is provided for the convenience of the reader to provide a basic understanding of such embodiments and does not wholly define the breadth of the disclosure. This summary is not an extensive overview of all contemplated embodiments and is intended to neither identify key or critical elements of all embodiments nor to delineate the scope of any or all aspects. Its sole purpose is to present some concepts of one or more embodiments in a simplified form as a prelude to the more detailed description that is presented later. For convenience, the term "certain embodiments" may be used herein to refer to a single embodiment or multiple embodiments of the disclosure.

Certain embodiments disclosed herein include a system for tracking items placed on one or more worksurfaces that comprises: one or more sensors, wherein at least a first sensors of the one or more sensors is an image sensor; a processing circuitry communicatively connected to the one or more sensors; and, a memory communicatively connected to the processing circuitry, wherein the memory further contains therein instructions that when executed by the processing circuitry configure the system to: receive task information; receive from at least one or more sensors an image of the one or more worksurfaces; identify content placed on the one or more worksurfaces by electronic analysis of the at least an image; compare the identified content to the received task information and perform a task-worksurface mismatch if an inconsistency is found, otherwise continue execution; track content of the one or more worksurfaces over time and compare to expected content at any given time based on the received task information and perform a task-worksurface discrepancy if a discrepancy is found, otherwise continue execution; determine whether the task has completed and if so, check content of the one or more worksurfaces against the expected end of task content based on the received task information; and, generate an alert upon the task completion if a discrepancy is found between the expected and actual content of the one or more worksurfaces is found. In these embodiments, worksurfaces include, for example, tables, benches, workspace, trays, containers, receptacles, pallets, and the like. In these embodiments, items may include, but are not limited to, instruments, tools, consumables and other matter that is required to perform, for example, a surgery, and any combinations thereof.

Certain embodiments disclosed herein also include a method for tracking items placed on one or more workspaces comprising: receiving task information; receiving from at least one or more sensors at least an image of the one or more workspaces; identifying content placed on the one or more workspaces by electronic analysis of at least an image; comparing the identified content to the received task information and perform a task-workspace mismatch if an inconsistency is found, otherwise continue execution; tracking content of the one or more workspaces over time and compare to expected content at any given time based on the received task information and perform a task-workspace discrepancy if a discrepancy is found, otherwise continue execution; determining whether the task has completed and if so, check content of the one or more workspaces against the expected end of task content based on the received task information; generating an alert upon the task completion if a discrepancy is found between the expected and actual content of the one or more workspaces is found. In these embodiments, worksurfaces include, for example, tables, benches, workspace, trays, containers, receptacles, pallets, and the like. In these embodiments, items may include, but are not limited to, instruments, tools, consumables and other matter that is required to perform, for example, a surgery, and any combinations thereof.

Furthermore, embodiments disclosed herein also include a non-transitory computer readable medium having stored thereon instructions for causing a processing circuitry to execute the process of tracking items placed on one or more workspaces comprising: receiving task information; receiving from at least one or more sensors at least an image of the one or more workspaces; identifying content placed on the one or more workspaces by electronic analysis of at least an image; comparing the identified content to the received task information and perform a task-workspace mismatch if an inconsistency is found, otherwise continue execution; tracking content of the one or more workspaces over time and compare to expected content at any given time based on the received task information and perform a task-workspace discrepancy if a discrepancy is found, otherwise continue execution; determining whether the task has completed and if so, check content of the one or more workspaces against the expected end of task content based on the received task information; generating an alert upon the task completion if a discrepancy is found between the expected and actual content of the one or more workspaces is found. In these embodiments, worksurfaces include, for example, tables, benches, workspace, trays, containers, receptacles, pallets, and the like. In these embodiments, items may include, but are not limited to, instruments, tools, consumables and other matter that is required to perform, for example, a surgery, and any combinations thereof.

BRIEF DESCRIPTION OF THE DRAWINGS

The subject matter disclosed herein is particularly pointed out and distinctly claimed in the claims at the conclusion of the specification. The foregoing and other objects, features, and advantages of the disclosed embodiments will be apparent from the following detailed description taken in conjunction with the accompanying drawings.

DETAILED DESCRIPTION

Figure 1:
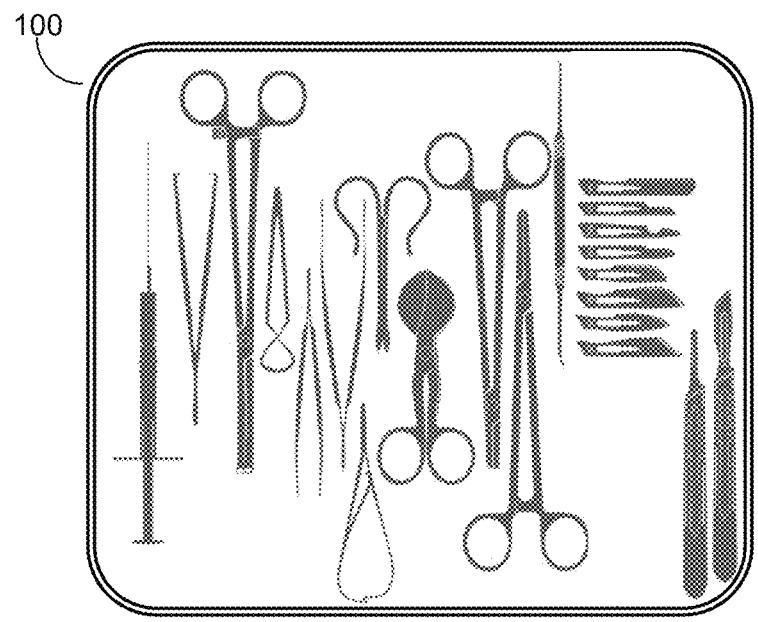
FIG. 1 is a worksurface containing thereon items to be used to perform a surgical task.

The embodiments disclosed by the disclosure are only examples of the many possible advantageous uses and implementations of the innovative teachings presented herein. In general, statements made in the specification of the present application do not necessarily limit any of the various claimed disclosures. Moreover, some statements may apply to some inventive features but not to others. In general, unless otherwise indicated, singular elements may be in plural and vice versa with no loss of generality. In the drawings, like numerals refer to like parts through several views.

Below, example embodiments will be described in detail with reference to accompanying drawings so as to be easily realized by a person having ordinary knowledge in the art. The example embodiments may be embodied in various forms without being limited to the example embodiments set forth herein. Descriptions of well-known parts are omitted for clarity, and like reference numerals refer to like elements throughout. Relative dimensions of elements in drawings may be exaggerated for clarity. Relative orientation of components and/or sub-components shown in the drawings may vary without departing from the scope of the disclosed embodiments.

According to an embodiment, a system includes a plurality of sensors adapted to identify and track items, e.g., tools, instruments and consumables, placed on worksurfaces. Each worksurface may contain one or more of these items and is used in an operating room. It is first determined if all the necessary items are available for a task at hand, then as items are removed, added or consumed a tally is updated to ensure that each is accounted for. When the task ends all items have to be accounted for by having the sensors review the content of the worksurfaces and identifying any discrepancy. In one embodiment, the system learns a process, e.g., a surgical process, such that in future cases it provides alerts of missing items before and after the task, provide instructions to equipment such as robots to assist in the task performance, and the like.

Figure 2:
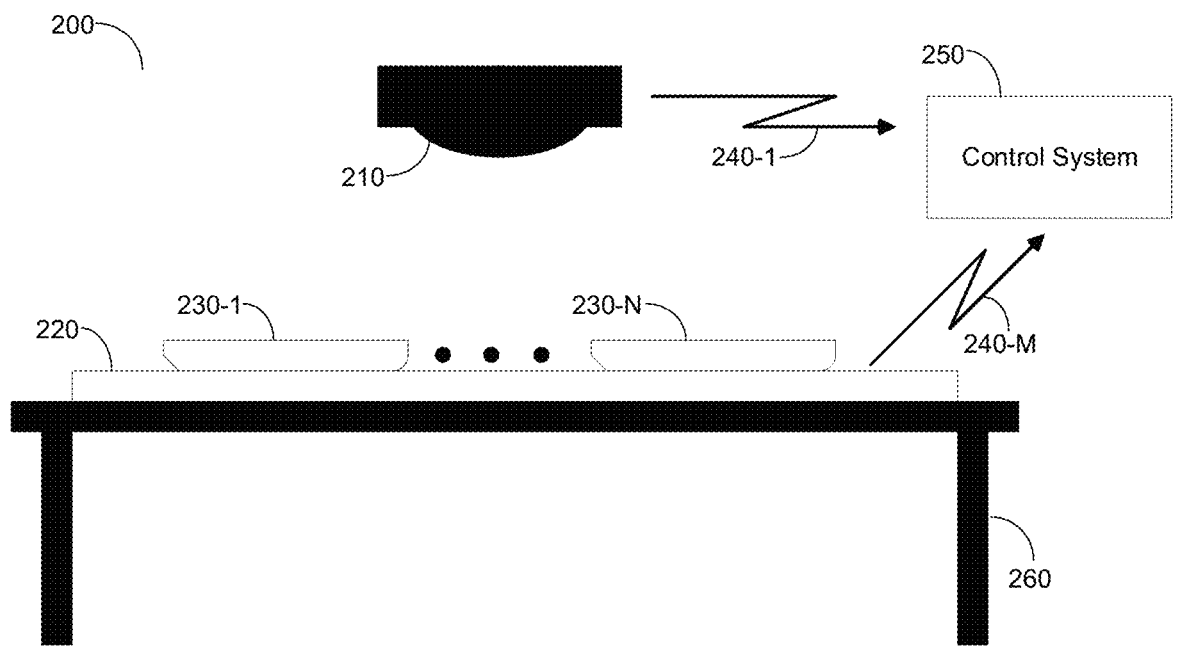
FIG. 2 is a schematic drawing of a system deployed for the purpose of learning, identifying and tracking items placed on worksurfaces according to an embodiment.

FIG. 2 depicts an example schematic drawing 200 of a system deployed for the purpose of learning, identifying and tracking items placed on worksurfaces according to an embodiment. Items may include, but are not limited to, instruments, tools, consumables and other matter that is required to perform, for example, a surgery, and any combinations thereof. Accordingly on a tabletop 260 there is placed a weight sensor surface 220, which may include one or more weight sensors (not shown and further discussed herein) embodied therein. Workspaces 230, for example workspaces 230-1 through 230-N, where N is an integer equal to or greater than '1', are placed on the weight sensor surface 220. Worksurfaces include, but are not limited to, tables, benches, workspace, trays, containers, receptacles, pallets, and the like. As a result, as workspaces are placed on or removed from the weight sensor surface 220, or as equipment, tools or consumables are removed or replaced within a workspace 230, for example workspace 230-1, the weight sensor surface 220 can sense the change in weight and report back as described herein. From above there is place a camera module 210, which may contain one or more images sensors (not shown and further discussed herein) of one or more types. These image sensors can continuously or periodically capture images, for example top-view images, of the workspaces 230 and report back as described herein. In an example embodiment, a communication hub 250, is communicatively connected to at least the weight sensor surface 220 and the camera module 210. Communication may be performed over communication links 240, for example communication links 240-1 through 240-M, where M is an integer equal to or great than '1'. The communication links 240 may be wired, such as a serial link, a bus, a network, and the like, or wireless, for example radio frequency (RF), such as WiFi®, Bluetooth®, Bluetooth low energy (BLE), WiLAN, and other like connections, as well as combinations thereof. The control system may then communicate to a processing system as further described herein.

Figure 3:
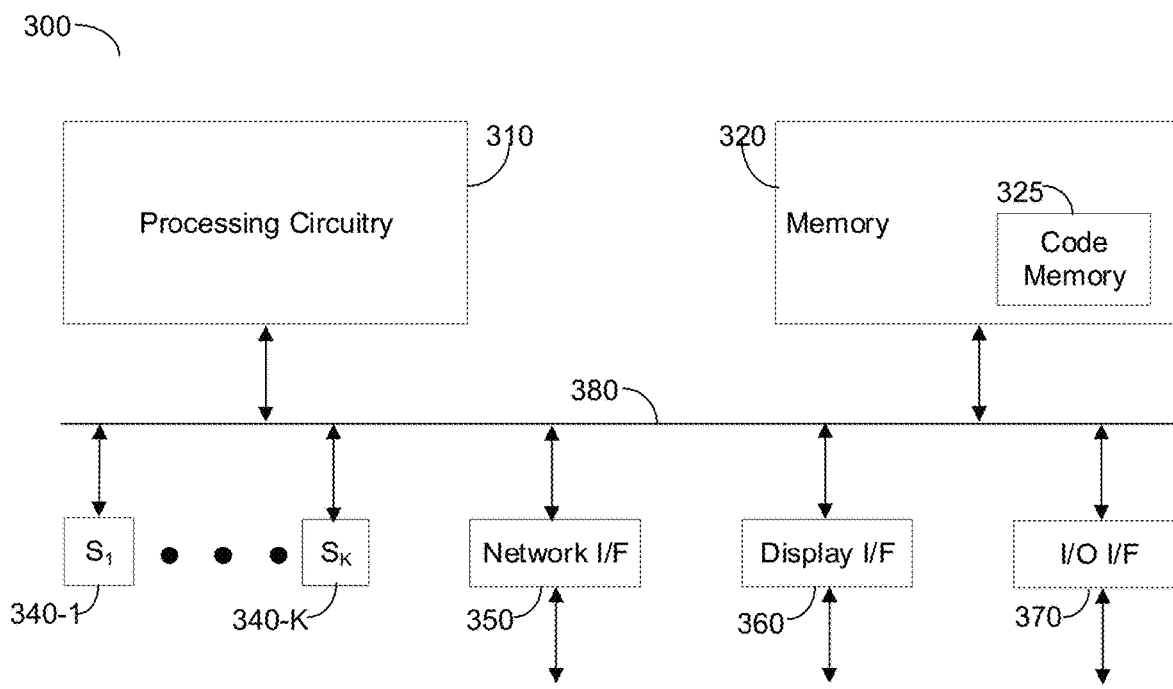
FIG. 3 is a system adapted to detecting content of one or more workspaces according to an embodiment.

FIG. 3 shows an example system 300 adapted to detecting content of one or more workspaces according to an embodiment. The system 300 comprises a processing circuitry 310 that may comprise one or more central processing units (CPUs), processing logic circuitry, controllers, microcontrollers, microprocessors and like devices, in any combination. The processing circuitry is communicatively connected to a communication link 380. The communication link 380 may be a serial communication link, a bus, a network (e.g., local area network (LAN), wide area network (WAN), and the like), whether wired or wireless, and any combinations thereof. To the communication link 380 there is connected a memory 320, the memory may comprise of both volatile memory (e.g., random access memory (RAM) and the like) or non-volatile memory (e.g., read only memory (ROM), Flash, ReRAM, and the like), and any combinations thereof. A portion of the memory 320 may be dedicated to a code memory 325, the code memory containing therein instructions that when executed by the processing circuitry 310 adapt the system 300 to perform as described herein.

For example, in an embodiment, and as further discussed herein, code contained in code memory 325 may be executed by the processing circuitry to initiate the training of a machine learning model to detect what is the content of each worksurface 230. It may be further trained to detect anomalies between an expected content of a worksurface and the actual content of the worksurface. For example, in the case of a particular surgical procedure, the machine learning model is trained to detect the set of tools, equipment and consumables expected to be present in one or more worksurfaces 230. It may be further trained to detect an anomaly at the end of a surgical procedure expecting to detect tools, equipment and consumables and detect anomalies with respect to expectations. In one embodiment such training of the machine learning module may include the update of instructions loaded into one or more robots operating in the theater so that when robots are used to assist in the performance of tasks they can provide the tooling as may be necessary, and as further explained herein.

To the communication link 380 there may be connected one or more sensors 340, for example sensors 340-1 through 340-K where K is an integer equal to or greater than '1', some of which are also described with respect of FIG. 2 herein. The sensors 340 may be of a variety of types including, but not limited to, weight sensors, image sensors, motion sensors, temperature sensors, proximity sensors, microphones, and the like, and any combinations thereof. Image sensors may include a range of sensors that include, but are not limited to, infra-red sensors, visible light, x-ray, and the like, and any combination thereof. A network interface 350 may be further connected to communication link 380 for the purpose of providing, for example but without limitation, to the Internet, the world-wide web (WWW) cloud and the like. The network interface 350 may comprise different wired and wireless network standards as well as proprietary networks, for both inter- and intra-organization communication networking. A display interface 360 may provide the system 300 with connectivity to one or more displays to allow the screening of information respective of the operation of the system 300 as further discussed herein. The system 300 may further comprise an input/output (I/O) interface 370 to allow connectivity to the likes of a mouse, a keyboard, a loudspeaker, and other like equipment associated or necessary for the proper operation of the system 300.

With respect to system 300, it may be adapted to use the sensors 340 to capture relevant information regarding routine tasks and automating an identified routine in, for example, an operating room. The system 300 is configured to identify a task and suggest recommendations or alerts to the performing operating room personal as needed. Such alerts may be provided via the display interface 360 by showing text or images on a screen (not shown) or make an announcement using voice commands over a loudspeaker (not shown) connected to the I/O interface 370, and so on.

It should be appreciated that the system 300 described herein may have different implementations, including without limitation, a distributed implementation. In some embodiments, the system 300 is a standalone system that is configured to perform the entire processing on its own. In other embodiments, and as further described herein, collaboration between different operating rooms within a site, across sits or across enterprises, is also possible.

Sensors 340 in the operating room may be installed as needed to collect raw data from areas of interest (e.g., above a working table, above a surgery table, monitoring the full room object and occupancy, etc.). All the collecting sensors 340 enrich the data collection of all the processes happening in the operating room. These may be identified by, for example, the machine learning process, a rule-based process, or by entry of a process being performed through the I/O interface 370. As operational supporting processes are not necessarily unified and may be different to various degrees between different medical teams, and further in order not to overload the teams with procedures or need to feed the system with detailed data, the system 300 may be configured to be a self-learning system utilizing techniques such as, but not limited to, computer vision and artificial intelligence (AI) system (e.g., machine learning). The system 300 is adapted to automatically learn relevant procedures within the operating room and is further configured to transform the data collected by the sensors 340 (images, sound, motion, wright, and more) into a structured detailed data.

The code of system 300, and in particular the code stored in code memory 325 may be further configured to provide immediate decisions via a support application in order to monitor and update the necessary information on the progress of the surgery supporting-operational processes. In an embodiment, such code in code memory 325 may further adapt the system 300 to enable the collection of reports and macro-data review in order to support purchasing and resource allocation issues as needed.

Figure 4:
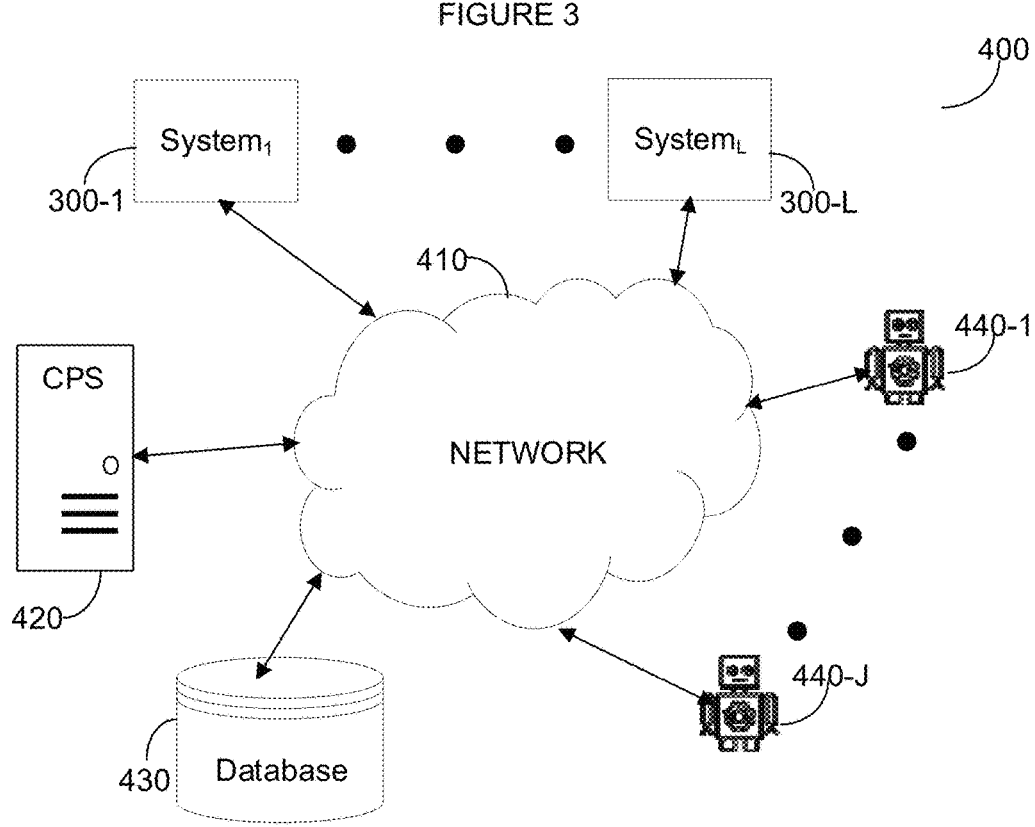
FIG. 4 is a diagram of a collaborative processing system according to an embodiment.

FIG. 4 depicts a diagram of an example collaborative system 400 according to an embodiment as shown. A network 410 provides the vehicle for communication between the elements connected thereto. The network 410 may be a local area network (LAN), a wide area network (WAN), and metro area network (MAN), the Internet, the world-wide web (WWW) and like communication networks, and combinations thereof. The network 410 may us different connectivity technologies which may include wired technologies over copper, fiber, and the like, or wireless technologies such as WiFi® or cellular, to name but a few, and any combination thereof. To the network 410 there are connected one or more of the systems 300, for example system 300-1 through system 300L, where L is an integer equal to or greater than '1'. Each of the system 300 may have all or part of the functionality describe with respect of FIG. 3, for example, system 300-1 may have two cameras but not weight sensors, while having code in the memory to perform a machine learning process, while a system 300-2 may be configured with ten cameras, a plurality of weight sensors, but the code in its memory does not have the machine learning capability.

Each of the system 300 is communicatively connected to the network 410 using, for example, its respective network interface 350. It should be further understood that the systems 300 may be positioned in operating rooms which are in proximity of each other, which are within a single enterprise, or across enterprise, each stage leading to a higher degree of collaboration.

To the network 410 there may be connected a collaborative processing server (CPS) 420 adapted to receive from each of the systems 300 information collected, processing that information, augmenting for missing capabilities in each of those systems, for example, providing machine learning capabilities, and providing feedback over the network to each of the system 300. It should be noted that the CPS 420, shown herein as a single unit, may comprise multiple processing circuitries which may be local or distributed, connected to each other via the network 410.

A database 430 communicatively connected to the network 410 may provide both storage for the systems 300 and the CPS 420, as well as contain data and information that may be retrieved by each of the systems 300 and the CPS 420. In an embodiment, one or more robots 440, for example robots 440-1 through 440-J, where J is an integer having a value of '0' or greater (when the value is '0' there are no robots in the system). The robots may receive periodic download of data as further discussed herein.

In an embodiment, real-time data collecting sensors 340, for example, camera module 210, are deployed over the area of interest and weight sensors are deployed underneath the tabletop 260 (such as, tables, trash canister and more). The stream of data collected is processed by a local server, for example processing circuitry 310 and memory 320, that in turn stream the analyzed data for analysis when needed. Such analysis may take place, for example, on CPS 420. On an embodiment, the computer vision operative on a system 300 or on the CPS 420 is used to automatically identify the objects placed on worksurfaces. Collected information may be used to correlate the computer vision information with the weight sensor outputs for enhanced accuracy of the image recognition process performance. As a result, a decision module executing on either a system 300 or the CPS 420 is adapted to report, for example, which instruments were taken out of the worksurfaces and needed to be returned before approving finishing the surgery; what specific devices that are missing out of the worksurfaces at any time; and, how many pads were inserted into the surgery area and how many were taken out.

In an embodiment, a data categorization module executing on either a system 300 or the CPS 420 is configured to transform and store the collected data into relevant operating room ontologies. The categorization module may be further adapted to create a list of used instruments, disposal devices or any other information collected to data sets from medical records or enterprise logistics information systems (not shown). Furthermore, a management and report module executing on either a system 300 or the CPS 420 is adapted to analyze relevant detections and actions during clinical operations into reports designed and created by either operation, clinical or logistics personnel within the enterprise.

In an embodiment, a module executing on either a system 300 or the CPS 420 is adapted to analyze long term data collected from multiple sites as well as from a variety of enterprises. A particular example may include, but is not limited to, medical teams and clinical procedures as well as aggregate meta-information collected from other hospital systems. The unified multi-site data is analyzed by the module using deep-learning and machine learning (ML) algorithms that creates the operation room practice know-how baseline for any type of procedure. The baseline analysis for the procedure can be downloaded back to system 300 to update one or more decision-making processes executed thereon, or for the control or monitoring of one or more robots such as robots 440.

In an embodiment, for each video frame captured by a camera of system 300, for example, camera 210, there is a set of object detection algorithms that process that frame. Each algorithm extracts the object bounding-box or its instance segmentation pattern. The system 300 generates object detection models. Those model outputs predictions for interesting objects in the frame. Objects can be, but not limited to, sterile instruments, radiation machines, people, patient bed, and every item in the operation room.

In an embodiment, each object that is detected using the object detection and localization is classified to one of a plurality of predefined objects that may, for example, but not by way of limitation, have a definition in database 430. In an embodiment, the identification is performed by use of machine learning techniques.

In an embodiment, the machine learning techniques include rendering a three-dimensional (3D) model of an operation room at every point in time. This may be performed done by fusion of a plurality of input tracks using, for example, some or all the sensors 340. The 3D model is based on a photogrammetry model of the scene and is based on pre-calculated calibration information of all cameras, for example, camera 210, within the operating room.

Figure 5:
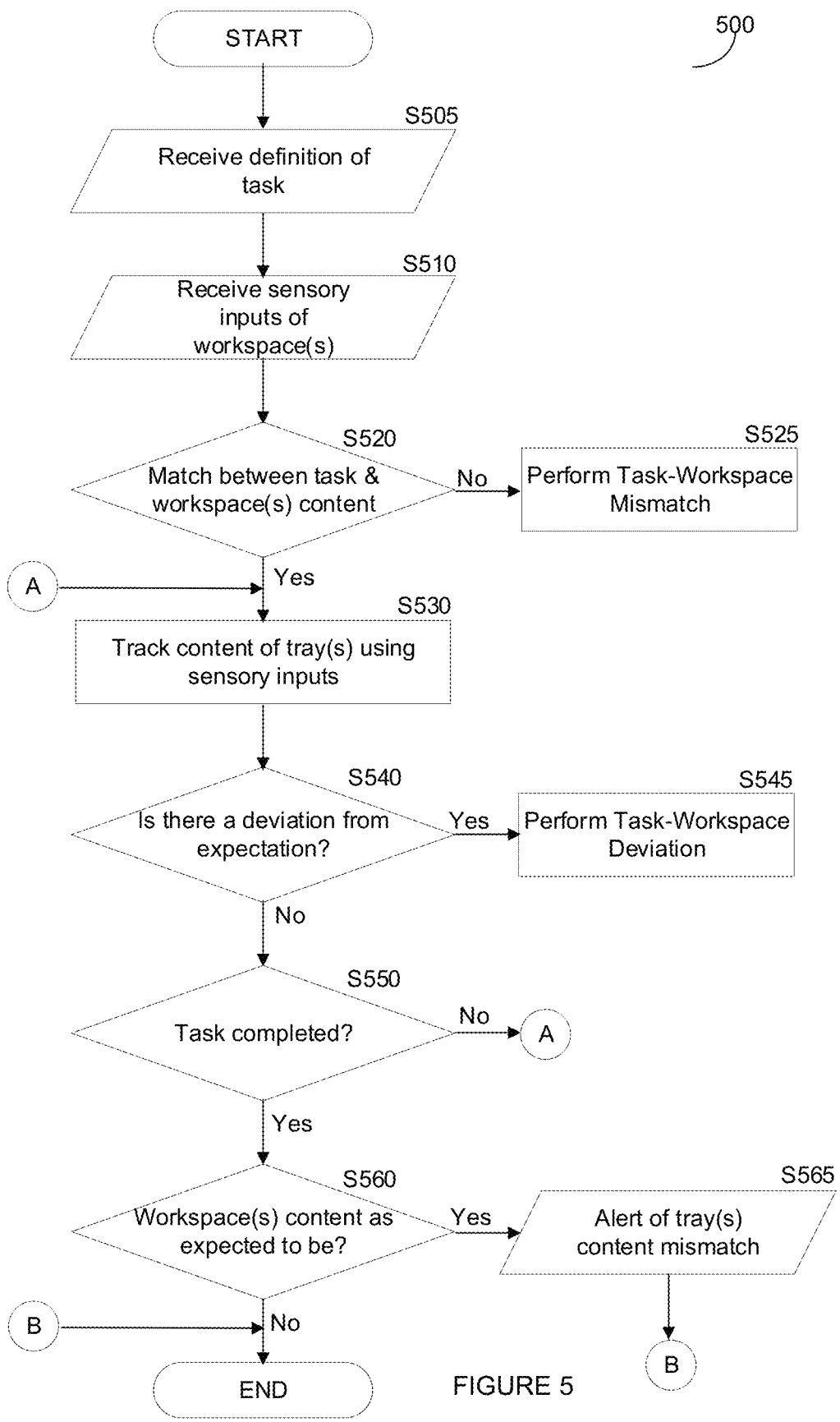
FIG. 5 is a flowchart of operation of the system according to an embodiment.

FIG. 5 depicts an example flowchart 500 of an operation of the system 300. The flowchart 500 is programmed for operation in the context of the collaborative system 400.

At S505 a task at hand is identified, for example, but not by way of limitation, a particular procedure that has to take place using various tools, equipment and consumables, and even more specifically, a surgery such as the removal of an appendix. By providing this information it is possible to use previously stored data, in either memory 320 or in database 430, as the case may be, for example as a reference to what is needed and expected in that particular procedure.

At S510 sensory information is received from one or more sensors, for example sensors 340. At S520 it is checked whether the sensory information received by checking one or more worksurfaces is consistent with the expectation for the task at hand, and if so execution continues with S530;

otherwise, executing continues with S525 where a task is performed, for example by executing instructions stored in memory 325, that when executed by the processing circuitry 310 adapted the system 300 to notify of the mismatch between the content of one or more of the worksurfaces and the expected content according to the task to be performed. S520 may be performed in a variety of ways, including, without limitation, by machine learning. A system 300 may execute by the processing circuitry 310 code stored in code memory 325, which represents a trained machine learning (ML) model. The trained ML model may be executed to identify content of worksurfaces, for example worksurfaces 230. In another embodiment computer vision technologies identify such content. Furthermore, combination of ML models and computer vision may be used to correctly identify the content of each worksurface and then compare the inventory on the worksurfaces to the expected content for the task, for example a surgical task, to ensure that all the necessary tools, equipment and consumables are present prior to commencement of the task.

In an embodiment training of an ML model further may take place for continuous improvement of the ML model detection capabilities. That is, the vector representing the content of items on the worksurfaces 230 is used to update the training set of the ML model in connection with the designated task, as a result, over time, an improved ML model may be generated.

At S530 the content of the worksurface or worksurfaces being monitored by the system 300 is checked by continuously receiving information from the sensors 340. Tracking of the content of the worksurfaces, for example worksurfaces 230, may be performed periodically or continuously using either an ML model, computer vision techniques or combinations thereof. The ML model may be trained to detect the normal flow of use of any of the items in the worksurfaces and upon detection of an anomaly, that is, a deviation from the expected view of items on the worksurfaces, provide the necessary information that may be used at S540 as described herein.

At S540 it is checked whether there exists a deviation from expectation between the content of the worksurface or worksurfaces and the expected content at any given stage of the process based, for example, on pre-existing information stored in memory 320 or in database 430. If no discrepancy is found, then execution continues with S550; otherwise, execution continues with S545 where a process to handle a task deviation is performed, that is, determining whether there actually is a problem or, if the deviation is within acceptable parameters. It is possible that an alert be provided, for example, but not by way of limitation, using the display interface 360 and showing certain content on a screen. In an embodiment an audio message may be played using the IO interface 370.

At S550 it is check if the task has completed and if so, execution continues with S560; otherwise, execution continues with S530. At S560 it is checked whether the content of the worksurface or worksurfaces is as expected at the end of the task and if not execution continues with S565 to provide alerts of a potential problem with missing items that should be on the worksurface at the end of the process, after which execution terminates; otherwise, if no discrepancy has been found, execution terminates. S560 may be performed using an ML model, computer vision techniques or any combinations thereof. An ML model may be trained to identify the expected items to be found in the worksurfaces, for example worksurfaces 230, at the end of the task, for example, a surgical procedure. A trained ML model may allow accounting for deviations between performance of the same task due to differences that may happen but are within the expected norm of the task. For example, an item may have to be placed in a body at surgery and therefore not returned to the worksurface while other must alert if accidently where not returned.

The various embodiments disclosed herein can be implemented as hardware, firmware, software, or any combination thereof. Moreover, the software is preferably implemented as an application program tangibly embodied on a program storage unit or computer readable medium consisting of parts, or of certain devices and/or a combination of devices. The application program may be uploaded to, and executed by, a machine comprising any suitable architecture. Preferably, the machine is implemented on a computer platform having hardware such as one or more central processing units ("CPUs"), a memory, and input/output interfaces. The computer platform may also include an operating system and microinstruction code. The various processes and functions described herein may be either part of the microinstruction code or part of the application program, or any combination thereof, which may be executed by a CPU, whether or not such a computer or processor is explicitly shown. In addition, various other peripheral units may be connected to the computer platform such as an additional data storage unit and a printing unit. Furthermore, a non-transitory computer readable medium is any computer readable medium except for a transitory propagating signal.

As used herein, the phrase "at least one of" followed by a listing of items means that any of the listed items can be utilized individually, or any combination of two or more of the listed items can be utilized. For example, if a system is described as including "at least one of A, B, and C," the system can include A alone; B alone; C alone; A and B in combination; B and C in combination; A and C in combination; or A, B, and C in combination.

It should be understood that any reference to an element herein using a designation such as "first," "second," and so forth does not generally limit the quantity or order of those elements. Rather, these designations are generally used herein as a convenient method of distinguishing between two or more elements or instances of an element. Thus, a reference to first and second elements does not mean that only two elements may be employed there or that the first element must precede the second element in some manner. Also, unless stated otherwise, a set of elements comprises one or more elements.

All examples and conditional language recited herein are intended for pedagogical purposes to aid the reader in understanding the principles of the disclosed embodiment and the concepts contributed by the inventor to furthering the art, and are to be construed as being without limitation to such specifically recited examples and conditions. Moreover, all statements herein reciting principles, aspects, and embodiments of the disclosed embodiments, as well as specific examples thereof, are intended to encompass both structural and functional equivalents thereof. Additionally, it is intended that such equivalents include both currently known equivalents as well as equivalents developed in the future, i.e., any elements developed that perform the same function, regardless of structure.

What is claimed is:
1. A system for tracking items placed on one or more worksurfaces, the system comprises:
one or more sensors, wherein at least a first sensor of the one or more sensors is an image sensor;

a processing circuitry communicatively connected to the one or more sensors; and a memory communicatively connected to the processing circuitry, wherein the memory further contains therein instructions that when executed by the processing circuitry configure the system to:

receive task information, the task information indicating a type of task to be performed using the items and acting as a reference as to what items are needed and expected over the course of the task to be performed;

receive from the one or more sensors an image of the one or more worksurfaces;

identify the items placed on the one or more worksurfaces by electronic analysis of the at least an image using image recognition of each of the items;

compare the identified items to the received task information and perform a task-worksurface mismatch if when an inconsistency is found, otherwise continue execution;

track the items of the one or more worksurfaces over time and compare to expected content at any given time based on the received task information and perform a task-worksurface discrepancy if a discrepancy is found, otherwise continue execution;

determine whether the task has completed and if so, check the items of the one or more worksurfaces against the items expected to be on the one or more worksurfaces at completion of the task based on the received task information; and generate an alert upon completion of the task when a discrepancy is found between the expected and actual items of the one or more worksurfaces is found.

2. The system of claim 1, wherein the memory further contains therein instructions that when executed by the processing circuitry configure the system to:
execute a machine learning model to identify the items placed on the one or more worksurfaces.

3. The system of claim 1, wherein the memory further contains therein instructions that when executed by the processing circuitry configure the system to:
execute at least a computer vision algorithm to identify the items placed on the one or more worksurfaces.

4. The system of claim 1, wherein the memory further contains therein instructions that when executed by the processing circuitry configure the system to:
execute a machine learning model to track the items of the one or more worksurfaces over time.

5. The system of claim 1, wherein the memory further contains therein instructions that when executed by the processing circuitry configure the system to:
execute at least a computer vision algorithm to track the items of the one or more worksurfaces over time.

6. The system of claim 1, wherein the memory further contains therein instructions that when executed by the processing circuitry configure the system to:
execute a machine learning model to check the items of the one or more worksurfaces against the expected end of task content based on the received task information.

7. The system of claim 1, wherein the memory further contains therein instructions that when executed by the processing circuitry configure the system to:
execute at least a computer vision algorithm to check content of the one or more worksurfaces against the expected end of task the items based on the received task information.

8. The system of claim 1, wherein the memory further contains therein instructions that when executed by the processing circuitry configure the system to perform at least one of: train a machine learning model to identify the items placed on the one or more worksurfaces, train a machine learning model to track the items of the one or more worksurfaces over time, and train a machine learning model to check the items of the one or more worksurfaces against the expected end of task items based on the received task information.

9. The system of claim 1, wherein the items are surgical items.

10. The system of claim 9, wherein the surgical items are at least one of: surgical instruments, surgical equipment, surgical consumables.

11. The system of claim 1, wherein the task information is information regarding a surgical procedure and the items associated therewith.

12. The system of claim 1, wherein the at least an image of the one or more worksurfaces is a top-view image of the one or more worksurfaces.

13. The system of claim 1, wherein a surface is at least one of: a table, a bench, a workspace, a tray, a container, a receptacle, a pallet.

14. A method for tracking items placed on one or more worksurfaces comprising:
receiving task information, the task information indicating a type of task to be performed using the items and acting as a reference as to what items are needed and expected over the course of the task to be performed;
receiving from at least one or more sensors at least an image of the one or more worksurfaces;
identifying the items placed on the one or more worksurfaces by electronic analysis of the at least an image using image recognition of each of the items;
comparing the identified items to the received task information and perform a task-worksurface mismatch when an inconsistency is found, otherwise continue execution
tracking the items of the one or more worksurfaces over time and compare to expected content at any given time based on the received task information and perform a task-worksurface discrepancy if a discrepancy is found, otherwise continue execution;
determining whether the task has completed and if so, check the items of the one or more worksurfaces against items expected to be on the one or more worksurfaces at completion of the task based on the received task information; and
generating an alert upon completion of the task when a discrepancy is found between the expected and actual items of the one or more worksurfaces is found.

15. The method of claim 14, further comprising:
executing a machine learning model to identify the items placed on the one or more worksurfaces.

16. The method of claim 14, further comprising:
executing at least a computer vision algorithm to identify the items placed on the one or more worksurfaces.

17. The method of claim 14, further comprising:
executing a machine learning model to track the items of the one or more worksurfaces over time.

18. The method of claim 14, further comprising:
executing at least a computer vision algorithm to track the items of the one or more worksurfaces over time.

19. The method of claim 14, further comprising:
executing a machine learning model to check the items of the one or more worksurfaces against the expected end of task items based on the received task information.

20. The method of claim 14, further comprising:
executing at least a computer vision algorithm to check the items of the one or more worksurfaces against the expected end of task content based on the received task information.

21. The method of claim 14, further comprising:
training a machine learning model to identify the items placed on the one or more worksurfaces.

22. The method of claim 14, further comprising:
training a machine learning model to track the items of the one or more worksurfaces over time.

23. The method of claim 14, further comprising:
training a machine learning model to check the items of the one or more worksurfaces against the expected end of task items based on the received task information.

24. The method of claim 14, wherein the items are surgical items.

25. The method of claim 24, wherein the surgical items are at least one of: surgical instruments, surgical equipment, surgical consumables.

26. The method of claim 14, wherein the task information is information regarding a surgical procedure and the items associated therewith.

27. The method of claim 14, wherein the at least an image of the one or more worksurfaces is a top-view image of the one or more worksurfaces.

28. The method of claim 14, wherein a surface is at least one of: a table, a bench, a workspace, a tray, a container, a receptacle, a pallet.

29. A non-transitory computer readable medium having stored thereon instructions for causing a processing circuitry to execute the process of claim 14.

* * * * *